United States Patent [19]

Kawakami et al.

[11] Patent Number: 4,490,436

[45] Date of Patent: Dec. 25, 1984

[54] POLYMER FILLER PARTICLES WITH FILLER FREE COATING

[75] Inventors: Masato Kawakami, Sagamihara; Seiji Tai, Yokohama, all of Japan

[73] Assignee: Japan Synthetic Rubber Co., Ltd., Tokyo, Japan

[21] Appl. No.: 435,666

[22] Filed: Oct. 21, 1982

[30] Foreign Application Priority Data

Oct. 30, 1981 [JP] Japan .............................. 56-173799

[51] Int. Cl.³ ............................................. B01J 13/02
[52] U.S. Cl. .................................. 428/403; 428/405; 428/407; 424/20; 424/22
[58] Field of Search ....................... 428/403, 405, 407; 128/1.3; 424/20, 22

[56] References Cited

U.S. PATENT DOCUMENTS

| | | | |
|---|---|---|---|
| 3,639,306 | 2/1972 | Steinberg et al. | 428/407 X |
| 3,650,814 | 3/1972 | Elder, Jr. | 428/407 X |
| 3,909,444 | 9/1975 | Anderson et al. | 428/407 X |
| 3,922,379 | 11/1975 | Farhadieh | 428/407 X |
| 4,061,828 | 12/1977 | Mazarguil et al. | 428/407 X |
| 4,331,654 | 5/1982 | Morris | 128/1.3 X |
| 4,345,588 | 8/1982 | Widder et al. | 128/1.3 |

Primary Examiner—Marion E. McCamish
Assistant Examiner—Nancy A. B. Swisher
Attorney, Agent, or Firm—Oblon, Fisher, Spivak, McClelland & Maier

[57] ABSTRACT

A polymer particle produced by forming a layer of filler-free polymer (II) on the surface layer of a filler-containing polymer particle (I) by polymerization of a monomer composed mainly of an ethylenically unsaturated compound in the presence of the polymer particle (I) is suitable for uniformly carrying a biological substance such as an immunoreactive substance, enzyme or cell on its surface because it has no filler in its surface layer, and the physical properties of the filler contained in the polymer particle (I) can be utilized.

21 Claims, No Drawings

POLYMER FILLER PARTICLES WITH FILLER FREE COATING

This invention relates to a polymer particle wherein a layer of filler-free polymer is formed on the surface of a filler-containing polymer particle.

Filler-containing particles are used in many fields such as electrophotography, coating material, ink, ion exchange resin, molded resin, carrier for biological substance, and carrier for administration of medicine.

Hitherto, filler-containing polymer particles have been produced, for example, by the suspension polymerization of a monomer mixture containing a filler (Japanese Patent Application Kokai (Laid-Open) No. 55,406/81).

However, since such filler-containing polymer particles are produced by suspension polymerization, they are restricted in various respects such as kind of monomer, amount of monomer, and so on. Usually, the physical properties of the filler existing in the inner part of the polymer particle are utilized. However, in some cases, it is required that the surface of polymer particle is composed only of polymer. For example, when the polymer particles are used as a carrier for adsorbing or combining a biological substance such as an immunoreactive substance, enzyme or cell, conventional filler-containing polymer particles are not suitable for carrying the above-mentioned substances uniformly on their surfaces because fillers are distributed even on their surfaces.

The object of this invention consists in providing a polymer particle wherein a filler exists in the inner part of the polymer particles and does not exist on the surface of the polymer particle.

According to this invention, there is provided a polymer particle consisting of a filler-containing polymer particle (I) and a layer of a filler-free polymer (II) formed on the surface of the filler-containing polymer particle (I) by polymerizing a monomer composed mainly of an ethylenically unsaturated compound.

Though the composition of the monomer for forming the filler-containing polymer particle (I) is not critical, it is usually composed of an ethylenically unsaturated compound.

As said ethylenically unsaturated componnd, there may be used aromatic alkenyl compounds such as styrene, α-methylstyrene, vinyltoluene, halogenated styrenes and the like; α,β-ethylenically unsaturated carboxylic esters such as alkyl esters of acrylic and methacrylic acids having a $C_1$–$C_8$ alkyl group (for example, methyl, ethyl, propyl, butyl and 2-ethylhexyl groups); alkenyl cyanides such as acrylonitrile, methacrylonitrile and the like; vinyl halides such as vinyl chloride, vinyl bromide and the like; and vinyl esters of straight and branched chain fatty acids such as acetic acid, propionic acid, butyric acid and the like. These compounds may be used alone or in admixture of two or more. Among these ethylenically unsaturated compounds, preferable are styrene, methyl methacrylate, ehtyl acrylate, butyl acrylate, 2-ethylhexyl acrylate, glycidyl methacrylate and acrylonitrile. The above-mentioned ethylenically unsaturated compound may be copolymerized with α,β-ethylenically unsaturated carboxylic acid or acids.

As said α,β-ethylenically unsaturated carboxylic acid, there may be used unsaturated monocarboxylic acids such as acrylic acid, methacrylic acid and the like; unsaturated dicarboxylic acids such as itaconic acid, maleic acid, fumaric acid and the like; monoalkyl esters of unsaturated dicarboxylic acids such as monomethyl itaconate, monoethyl maleate and the like; and so on. They can be used either alone or in admixture of two or more. Among these α,β-ethylenically unsaturated carboxylic acids, preferable are acrylic acid, methacrylic acid and itaconic acid. The amount of these acids copolymerized is usually 5% by weight or less. There may also be copolymerized, together therewith, a polyfunctional monomer such as divinylbenzene, vinyl methacrylate; a polyester of (meth)acrylic acid with polyol (for example, ethylene glycol, polyethylene glycol); other monomers such as acrylamide, methacrylamide, N-methylolacrylamide, 2-hydroxyethyl (meth)acrylate, or the like. Said polyfunctional monomers or said other monomers may be used alone or in combination. The amount of said polyfunctional monomer or said other monomer copolymerized is preferably up to 10% by weight. It is also allowable to copolymerize the above monomer or monomers in admixture with a conjugated diene compound or the like, for example, butadiene, isoprene, piperylene and the like, in such an amount as not to cause aggregation and adhesion of the resulting filler-containing polymer particles (I) to one another, for example, 10% by weight or less.

The method of producing the filler-containing polymer particle (I) is not critical. For example, in carrying out suspension polymerization of one or more of the above-mentioned monomers in the aqueous phase in the presence of a polymerization initiator, a filler and a suspension protector and optionally in the presence of a chain transfer agent as mentioned in Japanese Patent Application Kokai (Laid-Open) No. 55,406/81, said filler is dispersed in a solution prepared by dissolving at least one water-insoluble (co)polymer in said monomer, the resulting dispersion of the filler in the monomer solution is suspended in water, and the monomer is then polymerized, whereby the filler-containing polymer particle (I) is obtained.

Said polymerization initiator is appropriately selected from organic solvent-soluble polymerization initiators conventionally used in radical polymerization. Examples of usable polymerization initiator include acyloyl peroxides such as benzoyl perioxide, lauroyl peroxide and the like; aralkyl hydroperoxides such as cumene hydroperoxide, p-menthane hydroperoxide and the like; alkyl esters of peracids such as t-butyl perbenzoate, i-propyl peracetate and the like; dialkyl peroxides such as di-t-butyl peroxide and the like; and azobisacylonitriles such as azobisisobutyronitrile, azobiscyclohexanecarbonitrile and the like. These polymerization initiators are used usually in an amount of 0.1–5 parts by weight, preferably 0.5–3 parts by weight, per 100 parts by weight of the monomer.

As said chain transfer agent, these may be used, for example, straight chain and branched chain alkylmercaptans, halogenated hydrocarbons and the like. Usually, said chain transfer agent is added in an amount of 5 parts by weight or less per 100 parts by weight of the monomer.

Said suspension protector is used for the purpose of protecting the suspension state of monomer in the aqueous phase. Examples of organic suspension protector usable in this invention include synthetic, hydrophilic, high-molecular weight substances such as polyvinyl alcohol, polyvinyl pyrrolidone, polyethylene glycol and the like; naturally occurring, hydrophilic, high-molecular weight substances such as gelatin, water-soluble starch and the like, and semi-synthetic, hydrophilic, high-molecular weight substances such as carboxymethyl cellulose and the like. Examples of inorganic suspension protector usable in this invention include phosphates of magnesium, barium or calcium, as well as calcium carbonate, magnesium carbonate, zinc oxide, aluminum oxide, aluminum hydroxide and the like. These suspension protecters may be used in combination with a nonionic, anionic or cationic surfactant. Usually, these suspension protecters are used in an amount of 0.05–30 parts by weight per 100 parts by weight of the monomer. When a surfactant is used in combination with them, usually 2 parts by weight or less of the surfactant is used per 100 parts by weight of the monomer.

As the water-insoluble (co)polymer to be dissolved in the monomer in carrying out suspension polymerizaton, there may be used (co)polymers of the above-mentioned ethylenically unsaturated compounds.

Examples of the fillers usable in this invention include metals such as nickel, cobalt, copper, aluminum and the like; alloys formed of these metals; alloys formed of these metals and other metals such as the lanthanum series elements, for example, lanthanum, gadolinium and the like; metal oxides such as iron oxide, cobalt oxide, lead oxide, aluminum oxide, zinc oxide, silicon oxide, titanium oxide and the like; metal salts such as magnesium carbonate, calcium carbonate, aluminum silicate, barium sulfate, lead carbonate, lead chromate, cobalt aluminate, mercurous chloride and the like; metal sulfides such as zinc sulfide, cadmium sulfide and the like; pigments or metallic chelate compounds such as Nickel Metallized Azo Yellow, Red Lake R, Permanent Red 2B, Copper Phthalocyanine Blue, Copper Phthalocyanine Green and the like. The particle diameter of filler must be smaller than that of filler-containing polymer particle (I). Preferably, it is about 30 Å to 10 μm.

Since the surfaces of these fillers are hydrophilic, the fillers agglomerate mutually in an oily monomer in many cases, and the fillers are difficult to disperse uniformly in the oily monomer. Thus, the distribution of filler in filler-containing polymer particle (I) tends to become uneven.

Accordingly, in order to produce the filler-containing polymer paticle (I) having a uniform distribution of filler, it is preferable to employ a process for the suspension-polymerizateion of a filler-containing monomer in water in the presence of a polymerization initiator and a suspension protecter, in which a filler which has been treated so as to impart an oleophilic property to its surface and which does not agglomerate in the oily momoner is used as said filler. According to this process, the filler can uniformly be dispersed in the oily monomer, because a filler, to the surface of which an oleophilic property has been imparted, is used.

As the treatment method for imparting an oleophilic property to the surface of filler, there may be used, for example, a method for imparting an oleophilic property to the surface of filler which comprises contacting a filler with a surfactant composed mainly of a fatty acid in a medium such as water to form an adsorbed layer of the surfactant composed mainly of a fatty acid on the surface of the filler, followed by washing the filler with an acidic solution having a pH value of less than 7, preferably a pH value of not less than 5 and less than 7 (Japanese Patent Kokai (Laid-Open) No. 22,688/76). The surfactant composed mainly of a fatty acid used for this purpose includes alkali metal salts of unsaturated fatty acids such as rosin acid, dodecenic acid, tetradecenic acid, hexadecenic acid and the like; alkali metal salts of saturated fatty acids such as myristic acid, palmitic acid, stearic acid, arachic acid and the like; alkaline earth metal salts of rosin acid; and the like.

As the acidic solutions having a pH value of less than 7, there may be used solutions prepared by adjusting the pH of a lower alcohol such as methanol, ethanol or the like, a lower ketone such as acetone, methyl ethyl ketone or the like, water or the like with a mineral acid such as hydrochloric acid, sulfuric acid, nitric acid, phosporic acid or the like.

The treatment temperature for forming an adsorbed layer of a surfactant composed mainly of a fatty acid on the surface of filler is usually 30°–150° C., preferably 70°–110° C. The treatment time is usually 0.5–2 hours, preferably 0.5–1 hour. Though the concentration of a surfactant composed mainly of fatty acid in the dispersion medium is not critical, it is usually 0.2% by weight or more, preferably 1–20% by weight.

It is considered that the filler treated by this method has formed thereon a fatty acid layer, where the hydrophilic group of the fatty acid is adsorbed on the filler surface and its oleophilic group faces outside, so that an oleophilic property is imparted to the filler surface.

As another treatment method for imparting an oleophilic property to the filler, there is a method which comprises contacting a filler with a compound having a very high filler-affinity portion and an oleophilic portion in its molecule, bonding the high filler-affinity portion to the filler by adsorption or chemical combination and treating the filler so as to direct the oleophilic portion to outside. As such a compound, there may be used silane coupling agents represented by the formula (1):

wherein R is an alkoxy group preferably having 1–3 carbon atoms; an acyloxy group preferably having 2–4 carbon atoms, or a halogen; R' is a substituted or unsubstituted alkyl, alkenyl or aryl group, which includes, for example, $-(CH_2)_3NH_2$, $-(CH_2)_3SH$, $-(CH_2)_3-NH-C_2H_5$, $-(CH_2)_3NH-(CH_2)_2NH_2$, $-CH=CH_2$,

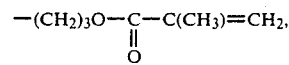

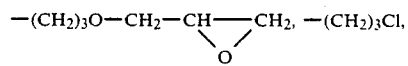

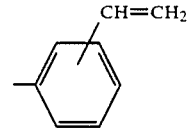

and the like; and n is 1, 2 or 3; titanate coupling agents represented by the formula (2):

wherein R" is a substituted or unsubstituted alkoxy or acyloxy group, said alkoxy having preferably 1–6 carbon atoms, said acyloxy having preferably 2–12 carbon atoms, particularly preferably 2–4 carbon atoms, which includes, for example, $CH_3O-$, $C_2H_5O-$, $C_3H_7O-$, $C_4H_9O-$, $CH_3C(CH_3)HO-$,

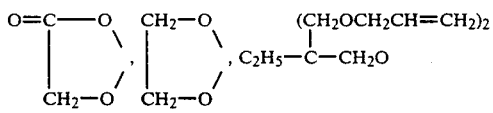

and the like;

R''' is an alkylacyloxy group having preferably 2-20 carbon atoms, a substituted benzene-sulfoxy group, a substituted phenoxy group, an unsaturated acyloxy group having preferably 2-6 carbon atoms, an alkyl phosphate group or an alkyl phosphite group, which include, for example,

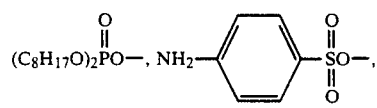

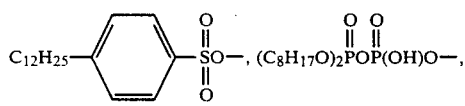

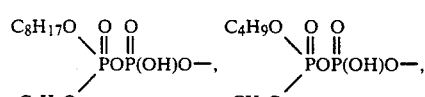

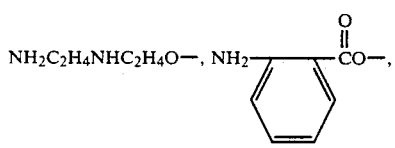

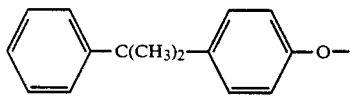

and the like; and m is 1, 2 or 3.

As the method for bonding a silane coupling agent or a titanate coupling agent to the filler, there may be used, for example, a method which comprises mixing the filler and the silane coupling agent or the titanate coupling agent in an inorganic medium such as water or the like or an organic medium such as an alcohol, an ether, a ketone, an ester or the like, heating the resulting mixture with stirring, thereafter separating the filler by means of decantation or the like and then removing the inorganic or organic medium by drying under reduced pressure or the like. The silane coupling agent or the titanate coupling agent may be bonded to the filler by directly mixing the filler with the silane coupling agent or the titanate coupling agent without using any inorganic or organic meidum and then heating the resulting mixture. In these methods, the heating temperature is usually 30°-100° C., and the heating time is about 30 minutes to 2 hours. Though the proportion of silane coupling agent or titanate coupling agent to filler is appropriately selected in consideration of the surface area of filler, it is usually 1-50 parts by weight, preferably 2-30 parts by weight, of the silane coupling agent or titanate coupling agent per 100 parts by weight of the filler. When an inorganic or organic medium is used, the concentration of the silane coupling agent or titanate coupling agent in the medium is usually 1% by weight or more, though it is not critical.

As other methods for imparting an oleophilic property to the filler, there may be used a method which comprises pulverizing the filler to finer particles by means of a pulverizing machine such as a ball mill in a hydrophobic medium containing a compound having a surface active effect such as a fatty acid, an alkyl sulfate, an alkylarylsulfonic acid or the like, thereby imparting an oleophilic property to the filler; a method which comprises adding and mixing an aqueous dispersion of fine powder of filler produced by a wet process or the like in the above-mentioned hydrophobic medium containing a surfactant to obtain an emulsion, thereafter heating the emulsion to distill off the water, thereby imparting an oleophilic property to the filler; and a method which comprises pre-heating the above-mentioned hydrophobic medium containing a surfactant, adding and mixing an aqueous dispersion of fine powder of filler produced by a wet process or the like into the hydrophobic medium and simultaneously distilling off the water, thereby imparting an oleophilic property to the filler.

As a method for separating the filler having an oleophilic property obtained by these methods, from the hydrophobic medium, various methods may be used. For example, the filler can be precipitated by mixing the hydrophobic medium containing the filler having imparted thereto an oleophilic property with a lower alcohol miscible with the hydrophobic medium such as ethanol, propanol and the like, and the precipitated filler can be collected by filtration, decantation or the like.

The filler which has been treated by these methods to impart an oleophilic property can quite readily be dispersed in an oily monomer. The filler which has been treated to impart an oleophilic property is mixed with the monomer preferably in a proportion of 0.1-70% by weight, particularly preferably 5-50% by weight, based on the weight of the mixture of the monomer and the filler.

The suspension polymerization method in the case of using the filler which has been treated to impart an oleophilic property is not critical. However, there may be used, for example, a method which comprises mixing and stirring an organic phase consisting of a monomer, a filler, a polymerization initiator and an optionally used chain transfer agent and an aqueous phase consisting of water, a suspension protector and an optionally used surfactant at a temperature lower than the polymerization-initiating temperature, suspending the organic phase as fine droplets having a uniform particle diameter in the aqueous phase, and thereafter elevating the temperature of the suspension system with stirring to initiate the polymerization of the monomer. The particle diameter and particle diameter distribution of the filler-containing polymer particle (I) obtained by this method are governed by the stirring conditions before the start of polymerization, the kind and amount of suspension protecter, and the kind and amount of optionally used surfactant, so that a filler-containing polymer particle (I) having the desired particle diameter and particle diameter distribution can be obtained by appropriately combining these factors.

Though the proportion of aqueous phase to organic phase is not critical, the amount of the aqueous phase used is usually 100-2,000 parts by weight, preferably 200-1,000 parts by weight, per 100 parts by weight of the organic phase.

The polymerization temperature for polymerizing the monomer by elevating the temperature of the suspension system may be appropriately varied depending upon the kinds and amounts of the monomer to be polymerized and the polymerization initiator used. It is usually 50°-150° C., preferably 60°-100° C. The other suspension-polymerization conditions are the same as those in the above-mentioned suspension polymerization method.

The filler-containing polymer particle (I) after the polymerization can be separated by a procedure such as centrifugation or the like, and after the separation, the filler-containing polymer particle (I) is optionally washed with water, ethanol, acetone or the like.

The filler-containing polymer particle (I) thus obtained usually has an average particle diameter of 0.1-2,000 μm, preferably 0.1-400 μm.

A polymer particle in which a layer of a filler-free polymer (II) is coated on the surface of the filler-containing polymer particle (I) obtained by the above-mentioned processes can be produced by, for example, the following polymerization process.

The filler-containing polymer particle (I) is dispersed in an aqueous phase containing a polymerization initiator, after which a monomer constituting the polymer (II) is charged and polymerized either at once or continuously. Of course, the filler-containing polymer particle (I) and the monomer may also be mixed together and then dispersed in the aqueous phase. The filler-containing polymer particle (I) and the monomer are dispersed in the aqueous phase, followed by adding the polymerization initiator thereto. The polymerization initiator used for the production of polymer (II) includes radical polymerization initiators, for example, persulfates; peroxides such as hydrogen peroxide, metal peroxides and the like; acyloyl peroxides; aralkyl hydroperoxides; esters of peracids; azonitriles; so-called redox catalyst system formed by reacting a peroxide with a reducing agent in the presence of an iron salt; and the like.

As said reducing agent, there may be used acid sodium sulfite, sodium thiosulfate, sodium metabisulfite and the like. In addition to them, there may also be used polymerization adjuvants such as molecular weight regulator, for example, t-dodecylmercaptan, carbon tetrachloride, and the like; and chelating agent, for example, sodium ethylenediaminetetraacetate and the like.

An emulsifier may be used in an amount of 1 part by weight or less per 100 parts by weight of the monomer, though it is not always used. As said emulsifier, there may be used anionic surfactants such as sodium dodecylbenzenesulfonate, potassium oleate and the like; and nonionic surfactant such as polyoxyethylene lauryl ether, polyoxyethylene nonylphenyl ether and the like alone or in combination.

As the monomer constituting the polymer (II), there is mainly used the same ethylenically unsaturated compound as used for the production of the filler-containing polymer particle (I).

Optionally, a monomer having functional group may be added as a comonomer in order to impart chemically active functional groups to the surface of the final polymer particle. As said monomer having functional group, there may be used a monomer having —OH as a side chain such as 2-hydroxyethyl methacrylate and the like; a monomer having —COHN$_2$ such as acrylamide and the like; or a monomer having —NH$_2$ such as p-aminostyrene and the like. These monomers may be used alone or in combination of two or more. These monomers may be copolymerized in an amount of up to about 50% by weight. Though the pH at the time of polymerization is not critical, it is usually in the range of 2 to 10. Though the polymerization temperature is not critical so far as it falls in the temperature range in which usual polymerization is conducted, a temperature range of 30°-100° C. is preferred.

The weight proportion of the filler-containing polymer particle (I) to the polymer (II) (weight ratio (I)/(II)) is preferably 100/5-200, more preferably 100/5-150 and most preferably 100/20-100. When the amount of the polymer (II) is less than 5 parts by weight per 100 parts by weight of the filler-containing polymer particle (I), the whole of the surface of the filler-containing polymer particle (I) cannot always be covered with the polymer (II), so that the surface of the filler-containing polymer particle (I) exposes in some cases. If the amount of the polymer (II) exceeds 200 parts by weight per 100 parts by weight of the filler-containing polymer particle (I), the shell layer of the polymer (II) becomes so thick that a sufficient effect cannot be exhibited in the utilization of the properties of internal filler. Though the particle diameter of the polymer particle is not critical, it is preferably 0.1-3000 μm, more preferably 0.2-500 μm.

In the polymer particle of this invention, the physical properties of the filler contained in its inner part can be utilized, and the surface of the particle is composed of a layer of the filler-free polymer. As the polymer constituting the polymer particle surface, there may be used any of the nonpolar polymer and polar polymer having functional group, and these may freely be combined, so that the surface performances of the polymer particle can be exhibited sufficiently. For example, when a fine particle of a high density substance is used as filler, a polymer particle can be obtained which has a high apparent density and the surface of which is composed only of a filler-free polymer. Since such a polymer particle can easily be separated from the surrounding liquid medium by utilizing gravitational force or centrifugal force, it is quite useful particularly as a carrier fior biological substances. When a filler having magnetism is used, it becomes possible to separate the polymer particle by means of magnetic force or to allow the polymer particle to move in a liquid medium, in a living body or in a vessel by means of magnetic force. Thus, there can be provided, according to this invention, the polymer particle that the physical properties of the filler contained therein can be utilized and that the chemical properties of the polymer constituting the polymer particle surface can be varied depending upon the intended object. Further, since the polymer particle has a small particle diameter, its surface area per unit volume is great, so that the polymer particle is considered to be particularly ideal as a carrier, the polymer surface of which is utilized. Examples of the above-mentioned biological substances are immunoreactive substances typified by antigens and antibodies, for example, surface antigen of B type hepatits (HBs antigen), anti-HBS antibody, human chorionic gonadotropin (HCG antigen), anti-HCG antibody, immunoglobulin G, mycoplasma antigen, nucleic acid, nuclear protein, estrogen, anti-estrogen antibody and the like; enzymes such as glucose-isomerase, glucose-oxidase, α-amylase, papain, aminoacylase and the like; and cells necessitating a solid surface for growth such as fetal pneumonocyte, renal cell, fibroblast and the like. These substances may be selected appropriately in accordance with the object.

This invention will be illustrated in more detail below referring to Examples which are not by way of limitation but by way of illustration.

EXAMPLE 1

Four hundred milliliters of 20% by weight aqueous potassium oleate solution was added to 1 liter of water containing 100 g of $Fe_3O_4$ having an average particle diameter of 100 Å which had been prepared by a wet process, and the resulting mixture was stirred at 90° C. for 30 minutes. After cooling the mixture, its pH was adjusted to 6 with dilute hydrochloric acid. The agglomerated $Fe_3O_4$ particles were collected by filtration, washed with two 300-ml portions of water at 80° C. and then with two 300-ml portions of ethanol, and dried under reduced pressure.

Into a 2-liter, four-necked flask equipped with a stirrer, a reflux condenser, a dropping funnel and a thermometer was introduced 800 ml of 3% by weight aqueous polyvinyl alcohol solution. On the other hand, 300 g of styrene, 6 g of benzoyl peroxide, 3.0 g of t-dodecylmercaptan and 60 g of the $Fe_3O_4$ particles obtained above having an oleophilic property imparted by treatment with potassium oleate, were previously stirred at 3,000 r.p.m. with ice-cooling to mix them uniformly, and the mixture thus prepared was dropped into the above-mentioned four-necked flask through the dropping funnel while stirring the aqueous polyvinyl alcohol solution present therein. After dropping the mixture, the contents of the flask were stirred for an additional 30 minutes, and when the particle diameter of the organic phase reached 3.0 μm, the temperature thereof was elevated to 75° C. and polymerized. Thereafter, the unreacted monomer was recovered under reduced pressure, and the polymer particles were separated by centrifugation and washed with three 500-ml portions of hot water. Thus, 320 g of a filler-containing polymer particle (I) was obtained. As measured by means of a microscope, it had an average particle diameter of 3.0 μm.

Then, 100 g of the filler-containing polymer particle (I) obtained above was placed in a 1-liter, four-necked flask equipped with a stirrer, a reflux condenser, a dropping funnel and a thermometer, and the polymer particle was dispersed in 400 ml of water containing 1 g of potassium persulfate. After thoroughly replacing the air in the flask with nitrogen, the contents of the flask were heated to 80° C. by means of a water bath with stirring. A mixture consisting of 80 g of styrene and 0.5 g of t-dodecylmercaptan was then continuously dropped thereinto over a period of 3 hours. After dropping it, polymerization was continued for an additional 5 hours at 90° C. The polymerization conversion was 99%. The elements existing on the surface of the polymer particle thus obtained were examined according to ESCA (electron spectroscopy for chemical analysis) in the usual manner. As a result, there are shown only absorptions of carbon resulting from the polymer and of oxygen contained in the air adsorbed on the polymer surface, and no existence of iron element was indicated. This polymer particle was attracted by a magnet, and its average particle diameter was 3.7 μm.

EXAMPLE 2

In the same manner as in Example 1, a monomer mixture consisting of 60 g of styrene, 10 g of isoprene and 0.5 g of t-dodecylmercaptan was polymerized on 100 g of the filler-containing polymer particle (I) obtained in Example 1. The polymerization conversion was 60%. As measured by ESCA in the same manner as in Example 1, existence of carbon and oxygen was provided and existence of iron was not confirmed on the surface of the polymer particle. The polymer particle thus obtained was attracted by a magnet, and its average particle diameter was 3.4 μm.

EXAMPLE 3

Four hundred milliliters of 20% by weight aqueous sodium oleate solution was added to 1 liter of water containing 100 g of lead oxide particles having an average particle diameter of 200 Å, and the resulting mixtures was stirred at 90° C. for 30 minutes. After cooling the mixture, its pH was adjusted to 6 with dilute hydrochloric acid. The agglomerated lead oxide particles were collected by filtration, washed with two 300-ml portions of water at 80° C. and then with two 300-ml portions of ethanol, and dried under reduced pressure. Then, suspension polymerization was carried out in the same manner as in Example 1, except that the 60 g of $Fe_3O_4$ particle to which an olephilic property had been imparted was replaced with 100 g of the lead oxide particle obtained above to which an oleophilic property had been imparted by treatment with sodium oleate. As a result, 360 g of a filler-containing polymer particle (I) having an average particle diameter of 4.5 μm was obtained.

Using 100 g of this filler-containing polymer particle (I), polymerization reaction was carried out in the same manner as in Example 1, except that the 80 g of styrene used as monomer was replaced with 40 g of styrene and 10 g of acrylonitrile. The polymerization conversion was 98%. The polymer particle thus obtained was washed with water, dried, and then pressed at 150° C. for 10 minutes at a pressure of 200 kg/cm$^2$ to obtain a thin plate. Then, its density was measured by a density gradient tube method. As a result, the density of this polymer particle was 1.382.

As measured by ESCA in the same manner as in Example 1, existence of carbon and oxygen was proved and existence of lead was not confirmed on the surface of the polymer particle. The average particle diameter of the polymer particle was 5.2 μm.

EXAMPLE 4

A solution prepared by dissolving 35 ml of $(CH_3O)_3$-$Si(CH_2)_3$—OCO—$C(CH_3)$=$CH_2$ as a silane coupling agent in 200 ml of ethanol was dropped at room temperature with stirring into 1 liter of water containing 100 g of $Fe_3O_4$ having an average particle diameter of 100 Å which had been prepared by a wet process. The resulting mixture was heated under reflux with stirring for one hour. After cooling the mixture, it was added to 3 liters of ethanol with stirring, and the resulting precipitate was collected by filtration, washed with two 300-ml portions of ethanol and dried under reduced pressure. Then, suspension polymerization was carried out in the same manner as in Example 1, except that the 60 g of $Fe_3O_4$ particle to which an oleophilic property had been imparted by treatment with potassium oleate was replaced with 60 g of the above-mentioned $Fe_3O_4$ particle to which an olephilic property had been imparted by treatment with the silane coupling agent. As a result, 320 g of a filler-containing polymer particle (I) having an average particle diameter of 3.5 μm was obtained.

Then, 100 g of the filler-containing polymer particle (I) obtained above was introduced into a 1-liter, four-necked flask equipped with a stirrer, a reflux condenser, a dropping funnel and a thermometer, and dispersed in 400 ml of water containing 1 g of potassium persulfate. After thoroughly replacing the air in the flask with nitrogen, the contents of the flask were heated to 80° C. with stirring by means of a water bath. Then, a mixture consisting of 80 g of styrene and 0.5 g of t-dodecylmercaptan was continuously dropped thereinto over a period of 3 hours. After dropping it, polymerization was continued at 90° C. for an additional 5 hours. The polymerization conversion was 97%.

As measured by ESCA in the same manner as in Example 1, existence of carbon and oxygen was proved and existence of iron was not confirmed on the surface of the polymer particle. The polymer particle thus obtained was attracted by a magnet, and its average particle diameter was 4.3 μm.

EXAMPLE 5

A polymer particle (I) having an average particle diameter of 200 μm was produced by repeating the procedure of Example 1, except that the 3% by weight aqueous polyvinyl alcohol solution was replaced with 0.8% by weight aqueous polyvinyl alcohol solution, and the stirring speed of 3,000 r.p.m. was changed to 1,000 r.p.m.

Then, in the presence of 100 g of this polymer particle (I), 80 g of styrene was polymerized in the same manner as in Example 1. As a result, a polymer particle having an average particle diameter of 250 μm was obtained. As measured by ESCA, no existence of iron was confirmed on the surface of the polymer particle.

EXAMPLE 6

To 80 ml of MEM (a trade name for a medium of Nissui Seiyaku) containing 5% by weight of bovin embryoserum was added 0.5 g of the polymer particle obtained in Example 5. In the mixture was then suspended $4 \times 10^4$ V 79 cells (pneumal fibroblast of Chinese hamster). After allowing the suspension to stand for 4 hours in an atmosphere of air containing 5% by volume of carbon dioxide in order to attach the cells to the polymer particles, the cells were cultured for 7 days while slowly stirring the suspension with a teflon-made stirring rod. After completion of cultivation, a magnetic force was applied from outside of the culture vessel to collect the polymer particles to the bottom of the culture vessel, and then the vessel was inclined while maintaining the polymer particles in said state, whereby MEM was allowed to flow out. Then, the polymer particles were washed with phosphate buffer saline (—) solution, after which the polymer particles were collected to the bottom of the culture vessel and phosphate buffer saline (—) solution was allowed to flow out in the same manner as above. Then, 2 ml of 0.25% by weight phosphate buffer saline (—) solution of trypsin was added to peel off the cells from the surface of polymer particles, after which the polymer particles were collected to the bottom of vessel by magnetic force and the phosphate buffer saline (—) solution of trypsin was recovered in the same manner as above. The number of V 79 cells in this phosphate buffer saline (—) solution of trypsin was $3 \times 10^6$.

The result of this Example demonstrates the superiority of the polymer particle of this invention as a cell culture bed.

COMPARATIVE EXAMPLE 1

V 79 cells were cultured in the same manner as in Example 6, except that the 0.5 g of polymer particle was replaced with 0.5 g of the filler-conteining polymer particle (I) produced in Example 5. However, no proliferation of V 79 cell was observed in this cultivation.

EXAMPLE 7

In 0.5 ml of phosphate buffer solution was dispersed 200 mg of the polymer particle obtained in Example 1, and 0.4 ml of phosphate buffer solution containing about 100 μg/ml of anti-HBs antibody was added to the resulting dispersion. The resulting mixture was shaken at 15° C. for 16 hours. The particles were collected by means of a magnet, and the supernatant was separated off. The remaining particles were repeatedly washed with phosphate buffer solution three times to obtain polymer particles having the antibody carried thereon.

To the polymer particles was added 0.4 ml of diluted human serum containing HBs antigen, and the resulting mixture was subjected to reaction at 50° C. for one hour, and thereafter washed in the same manner as above.

Subsequently, 0.4 ml of phosphate buffer solution containing about 100 μg/ml of anti-HBs antibody combined with ureaperoxidase was added to the washed polymer particles, and the resulting mixture was subjected to reaction at 50° C. for one hour, and then washed in the same manner as above.

Subsequently, 0.1 ml of ureaperoxide and 0.1 ml of 1% phosphate buffer solution of o-phenylenediamine were added to the washed particles, and the resulting mixture was shaken at room temperature for one hour while shading the light, upon which the mixture was colored at a concentration corresponding to the amount of the antibody combined with ureaperoxidase. The absorbance was measured at a wavelength of 492 nm by means of a spectrophotometer to obtain the results shown in Table 1.

TABLE 1

| Human serum dilution ratio | Absorbance |
|---|---|
| 3 | 0.55 |
| 81 | 0.35 |
| Blank | 0.18 |

The blank in Table 1 means that no human serum was added.

As shown in Table 1, the polymer particle of this invention exhibits an excellent sensitivity in detection of HBs antigen. Moreover, the polymer particles of this invention can be collected easily by a magnet, and therefore, the particles can easily be washed.

COMPARATIVE EXAMPLE 2

The same procedure as in Example 7 was repeated, except that the 200 mg of the polymer particle was replaced by 200 mg of the filler-containing polymer particle (I) obtained in Example 1, to detect HBs antigen. The absorbances in this case are shown in Table 2. It can be seen therefrom that when the filler-containing polymer particle (I) was used, the absorbance was lower and the sensitivity was lower than in Example 7.

TABLE 2

| Human serum dilution ratio | Absorbance |
|---|---|
| 3 | 0.29 |
| 81 | 0.32 |
| Blank | 0.35 |

The blank in Table 2 has the same meaning as in Table 1.

What is claimed is:

1. A polymer particle admixed with a biological substance, said polymer particle consisting of:
   (1) a filler selected from the group consisting of a metal, metal alloy, metal oxide, metal salt, metal sulfide, pigment and metallic chelate compound,
   (2) an oleophilic surface layer upon said filler, whereby said filler does not agglomerate in an oily monomer,
   (3) a layer of polymer upon said oleophilic-surfaced filler, and
   (4) a layer of a filler-free polymer of an ethylenically unsaturated monomer upon the surface of the filler-containing polymer.

2. A polymer particle according to claim 1, wherein said polymer particle (I) is produced by suspension polymerization of a monomer composed mainly of an ethylenically unsaturated compound in the aqueous phase in the presence of a polymerization initiator, a filler and a suspension protector, in which said filler is dispersed in a solution of at least one water-insoluble (co)polymer in said monomer, the resulting dispersion of the filler in the (co)polymer solution in the monomer is suspended in water and the monomer is then polymerized.

3. A polymer particle according to claim 2, wherein said water-insoluble (co)polymer is a (co)polymer of at least one ethylenically unsaturated compound or a copolymer of an ethylenically unsaturated compound and an $\alpha,\beta$-ethylenically unsaturated carboxylic acid.

4. A polymer particle according to claim 1, wherein said polymer particle (I) is produced by suspension polymerization of a monomer composed mainly of an ethylenically unsaturated compound containing a filler in the presence of a polymerization initiator and a suspension protector.

5. A polymer particle according to claim 4, wherein said filler which has been treated so as to impart an oleophilic property to its surface is a filler which has been prepared by contacting a filler with a surfactant composed mainly of a fatty acid in a medium and then washing it with an acidic solution having a pH value of less than 7.

6. A polymer particle according to claim 4, wherein said filler which has been treated so as to impart an oleophilic property to its surface is a filler which has been treated with a silane coupling agent or a titanate coupling agent, or a mixture thereof.

7. A polymer particle according to claim 6, wherein said silane coupling agent is $R_{4-n}SiR'_n$ in which R is an alkoxy group, an acyloxy group or a halogen; R' is a substituted or unsubstituted alkyl, alkenyl or aryl group; and n is 1, 2 or 3.

8. A polymer particle according to claim 6, wherein said titanate coupling agent is $R'''_m TiR''_{4-m}$ in which R''' is a substituted or unsubstituted alkoxy or acyloxy group, R'' is an alkylacyloxy, substituted benzenesulfoxy, substituted phenoxy, unsaturated acyloxy, alkyl phosphate or alkyl phosphite group, and m is 1, 2 or 3.

9. A polymer particle according to claim 4, wherein said filler which has been treated so as to impart an oleophilic property to its surface is a filler which has been subjected to the treatment of being finely pulverized in a hydrophobic medium containing a compound having a surface active effect, a filler which has been subjected to the treatment of an aqueous dispersion of a filler being added to a hydrophobic medium containing a surfactant to emulsify the resulting mixture and thereafter the water is distilled off by heating, or a filler which has been subjected to the treatment of a hydrophobic medium containing a surfactant being previously heated and an aqueous dispersion of a filler is then added and mixed while distilling off the water.

10. A polymer particle according to claim 2 or 4, wherein said ethylenically unsaturated compound is at least one compound selected from the group consisting of aromatic alkenyl compounds, $C_{1-8}$alkyl acrylates or methacrylates, alkenyl cyanides, vinyl halides and vinyl esters of straight or branched chain fatty acids.

11. A polymer particle according to claim 10, wherein said ethylenically unsaturated compound is at least one compound selected from the group consisting of styrene, methyl methacrylate, ethyl acrylate, butyl acrylate, 2-ethylhexyl acrylate, glycidyl methacrylate and acrylonitrile.

12. A polymer particle according to claim 2 or 4, wherein said polymerization initiator is used in a proportion of 0.1–5 parts by weight per 100 parts by weight of the monomer.

13. A polymer particle according to claim 2 or 4, wherein said suspension protector is used in a proportion of 0.05–30 parts by weight per 100 parts by weight of the monomer.

14. A polymer particle according to claim 1, wherein said polymer particle is a polymer particle which has been formed by radical-polymerizing a monomer composed mainly of an ethylenically unsaturated compound with a polymerization initiator in the state that said monomer and said polymer particle (I) are dispersed in the aqueous phase.

15. A polymer particle according to claim 1, wherein said biological substance is an immunoreactive substance, an enzyme or a cell.

16. A polymer particle according to claim 1 wherein the particle diameter of said filler is 30 Å to 10 μm.

17. A polymer particle accoding to claim 1, wherein said filler-containing polymer particle (I) has an average particle diameter of 0.1–2,000 μm.

18. A polymer particle according to claim 1, wherein the weight ratio of the polymer particle (I) to the polymer (II) is 100/5 to 100/200.

19. A polymer particle according to claim 1, wherein the weight ratio of the polymer particle (I) to the polymer (II) is 100/5 to 100/150.

20. A polymer particle according to claim 1, wherein the weight ratio of the polymer particle (I) to the polymer (II) is 100/20 to 100/100.

21. A polymer particle according to claim 1, which has a particle diameter of 0.1 to 3,000 μm.

* * * * *